United States Patent
Jadhav et al.

(10) Patent No.: US 8,142,802 B2
(45) Date of Patent: Mar. 27, 2012

(54) INSECTICIDAL COMPOSITION WITH ENHANCED SYNERGISTIC ACTIVITY

(75) Inventors: Prakash Mahadev Jadhav, Mumbai (IN); Jaidev Rajnikant Shroff, Mumbai (IN)

(73) Assignee: United Phosphorus, Ltd., Mumbai (IN)

( * ) Notice: Subject to any disclaimer, the term of this patent is extended or adjusted under 35 U.S.C. 154(b) by 1746 days.

(21) Appl. No.: 10/970,726

(22) Filed: Oct. 22, 2004

(65) Prior Publication Data

US 2005/0142158 A1 Jun. 30, 2005

Related U.S. Application Data

(60) Provisional application No. 60/512,851, filed on Oct. 22, 2003, provisional application No. 60/512,920, filed on Oct. 22, 2003.

(51) Int. Cl.
*A01N 25/12* (2006.01)
*A01N 25/02* (2006.01)
*A01N 57/28* (2006.01)
*A01N 53/08* (2006.01)

(52) U.S. Cl. ........ 424/409; 424/405; 424/406; 514/120; 514/521

(58) Field of Classification Search ....................... None
See application file for complete search history.

(56) References Cited

U.S. PATENT DOCUMENTS 6,440,440 B1 * 8/2002 Meerpoel et al. ............. 424/405
2002/0115565 A1 * 8/2002 Asrar et al. .................. 504/100

FOREIGN PATENT DOCUMENTS

GB 2082913 * 3/1982
WO WO 02/37964 A1 5/2002

* cited by examiner

*Primary Examiner* — Neil Levy
(74) *Attorney, Agent, or Firm* — Yancy IP Law, PLLC

(57) ABSTRACT

An insecticidal composition of Acephate and Cypermethrin with enhanced synergistic activity. Preferably, the insecticidal composition includes 0.1 to 25% w/w Cypermethrin active ingredient and 0.5 to 75% w/w Acephate active ingredient along with other ingredients to make dry flow, low compact, dust free granules.

12 Claims, 1 Drawing Sheet

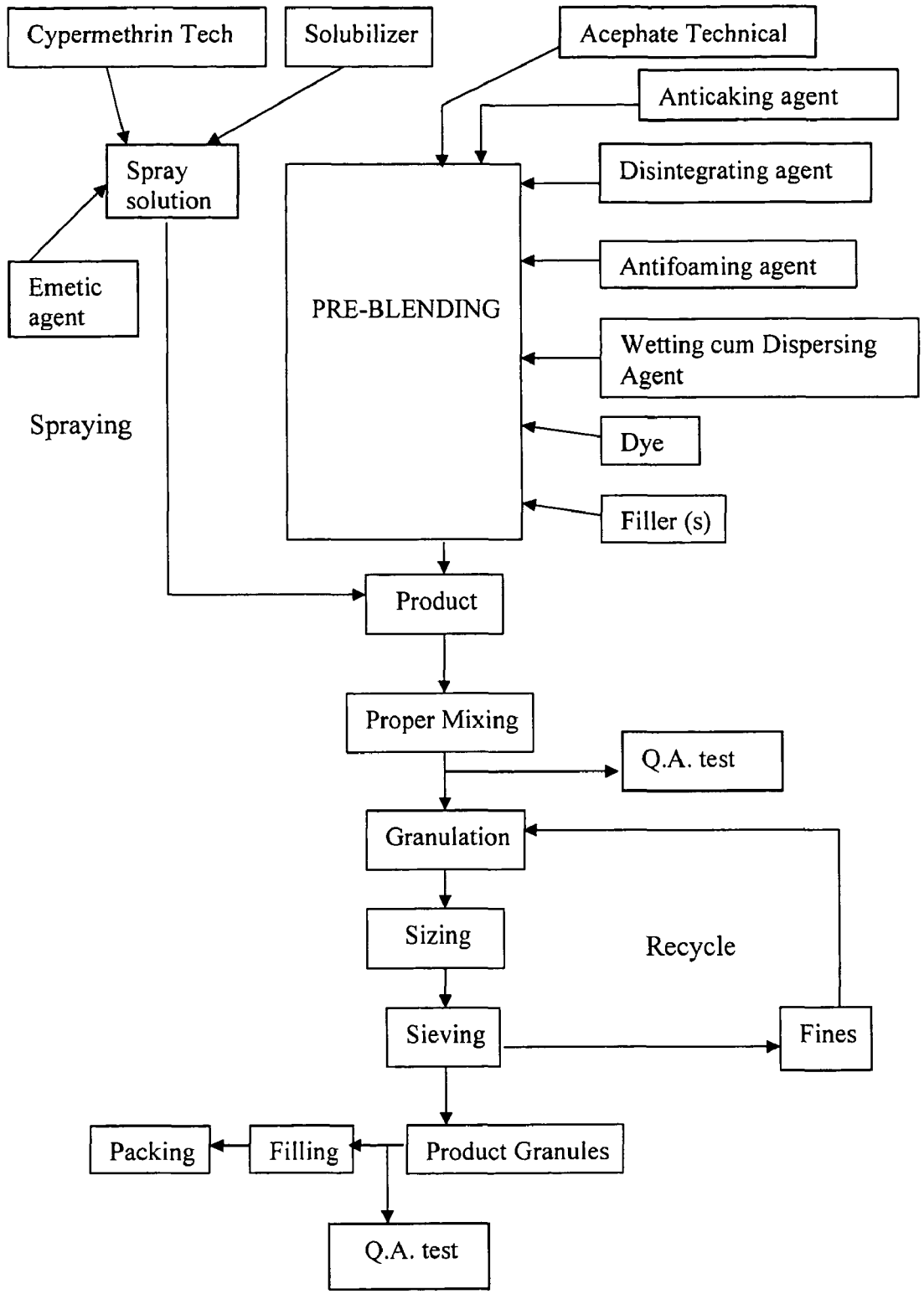

INSECTICIDAL COMPOSITION WITH ENHANCED SYNERGISTIC ACTIVITY

CROSS-REFERENCE TO RELATED APPLICATIONS

This application claims the benefit, under 35 U.S.C. 119(e), of U.S. Provisional Application No. 60/512,851 filed on Oct. 22, 2003 and U.S. Provisional Application No. 60/512,920 filed on Oct. 22, 2003, the contents of which are incorporated herein by reference.

BACKGROUND OF THE INVENTION

1. Field of the Invention

The present invention relates to an insecticidal composition of Cypermethrin and Acephate with enhanced synergistic insecticidal activity and a process to prepare the same.

2. Description of Related Art

The protection of crops and its produce from insect pest damage is essential in agriculture produce enhancement. To help combat these problems, various chemicals and formulations were invented for effective management of pests. Insecticides of many types and groups are reported in the literature and a large number are in use, commercially, for effective control of pests in agriculture.

In many cases, active insecticides have shown more effectiveness in combination than when applied individually. Synergism occurs when a combination demonstrates a potency and activity level exceeding that, which might be expected, from a mere addition of the individual potencies of the components.

In modern agricultural scenarios, insects have attained resistance, due to indiscriminate and non-judicious use of pesticide. Potent synergistic insecticidal composition would by useful to manage insect pests for a desired higher crop yield and to control those insects which are hard to kill by existing commercial insecticides solely and in cyclic spray mixtures.

Cypermethrin is presently recognized as a non-systemic insecticide with contact and stomach action. It also exhibits anti-feeding action and good residual activity on treated plants. It is used to control a wide range of insects, especially *Lepidoptera*, but also *Coleoptera, Deptera, Hemiptera* and other classes in fruits (including Citrus), Vines, Vegetables, Potatoes, Cucurbits, Lettuce, Capsicums, tomatoes, cereals, maize, soybeans, cotton, coffee, cocoa, rice, pecans, oilseeds rape, beet, ornamentals, forestry, etc. It is also used for control of flies, and other insects in animal houses, mosquitoes, cockroaches, houseflies and other insect pests in public. It is also used as an animal ectoparasiticide.

Presently Cypermethrin is most preferably formulated in the form of emulsifiable concentrate (EC) which consists of Cypermethrin active ingredients dissolved in solvent(s) along with surfactants at levels required to give maximum stability with the formation of a homogeneous emulsion on dilution. The use of organic solvent(s) is disadvantageous from an environmental and cost view point. These organic solvents exhibit toxicity and side-effects which may be adverse to the effect of the agricultural chemical itself or to the plant or crop as a whole or to its parts produced in treated fields. They show hazards during manufacturing, filling, packing, storage, transit and use. During use, dermal and respiratory toxic exposure to users is frequently observed. By using the organic solvents percutaneous toxicity and inflammability may also occur.

The formulation of Acephate presently in use is Acephate 75% Soluble Powder (SP) which consists of Acephate active ingredient 75% (w/w), surfactant 1% to 2% (w/w) and inert filler (Precipitated Silica) to make 100% (w/w). It poses problems like dust, low pourability, high transportation cost, and high capital manufacturing investment. This formulation is not easily measurable, presents difficulties in packing material disposal, produces handling problems, and poses a high risk of caking along with other problems.

Both of these compounds are capable of controlling a large spectrum of insects especially *Lepidoptera, Coleoptra, Diptera, Hemiptera* and others in classes such as fruits, vegetables, ornamentals, etc. Cypermethrin is distinguished for its sudden shock effect along with good residual activity on treated plants. Acephate is a systemic insecticide of moderate persistence with residual activity and thrips. It is phytotoxic on many crop plants.

A mixture of organophosphates and pyrethroids have been reported in literature, but these are applied as separate sprays or tank mixes. Formulations containing both are not reported.

BRIEF SUMMARY OF THE INVENTION

The present insecticidal composition with enhanced synergistic insecticidal activity includes the active ingredients Cypermethrin and Acephate along with necessary surface active agent(s) and inert filler(s). The present invention is also directed to a process for making dry flow, low compact, dust free granules including the insecticidal composition. In a preferred embodiment, the insecticidal composition including Cypermethrin and Acephate is prepared with the addition of a solubilizer, a wetting cum dispersing agent, a disintegrating agent, an emetic agent, an antifoaming agent, an anticaking agent, dye(s) and filler(s).

The beneficial results of each active ingredient, i.e. residual activity and anti-feeding action, are synergistically combined to yield an insecticidal composition of improved efficiency, in the form of higher yields. The amount of active ingredients, preferably mass of active ingredients per hectare, is significantly less than that required when these two active ingredients are utilized separately, under identical conditions. The chance of resistance development, which occurs when a single active ingredient is used for a long time and in high doses, is also reduced. The insecticidal composition also provides a ready-to-use, compatible plant-mix in an effective synergistic composition along with improving insecticidal activity.

The insecticidal composition including Cypermethrin and Acephate with enhanced synergistic insecticidal activity has a higher potentiation, as an insecticide, and is highly effective in controlling insect pests including even hard to kill pests. The present insecticidal composition gives a quick knockdown kill of the pests. It is comparatively more persistent and penetrates deep in leaves, killing many internal feeders. It is strongly active as a contact and stomach insecticide. It is especially a potent lethal weapon to kill hard-to-kill, resistant insect pests, which are normally not controlled by other insecticides. The insecticidal composition including Cypermethrin and Acephate has the beneficially effect for controlling Cotton bollworms and sucking pests. Its toxicity is low and safe for human and animals and its residue is small.

The present insecticidal composition minimizes dermal and respiratory toxic exposure to users and also eliminates percutaneous toxicity and flammability hazard since it does not contains any organic solvent. The insecticidal composition provided is relatively more advantageous and exhibits very desirable characteristics.

BRIEF DESCRIPTION OF THE DRAWING

The features and advantages of the present invention will become apparent from the following detailed description of a preferred embodiment thereof, taken in conjunction with the accompanying drawing, in which:

FIG. 1 is a flow chart showing the preferred process for preparing the insecticidal composition of the present invention.

DETAILED DESCRIPTION OF THE INVENTION

An insecticidal composition with enhanced synergistic insecticidal activity is produced by combining Cypermethrin and Acephate along with necessary surface active agent(s) and inert filler(s). The insecticidal composition preferably includes 0.1 to 25% w/w Cypermethrin and 0.5 to 75% w/w Acephate. In yet another preferred embodiment, the active ingredient Cypermethrin is present in a quantity of 0.1 to 10% w/w and the active ingredient Acephate is present in a quantity of 1.0 to 50% w/w. In yet another preferred embodiment, the ratio of Cypermethrin to Acephate in the insecticidal composition is 1:1 to 1:10, most preferably 1:9. Additionally, the Cypermethrin used may preferably include 45-80% cis-isomers.

Cypermethrin is an insecticide belonging to the synthetic pyrethroid group and describes a chemical substance having solubility in water of 0.004 mg/l (at pH7). Cypermethrin corresponds to a mixture of cis and trans isomers having the following formula:

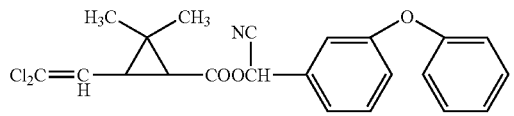

Cypermethrin is almost insoluble in water, but it is soluble in acetone, chloroform, cyclohexanone, xylene>450 g/l, ethanol 337 g/l, and hexane 103 g/l at 20° C.

Acephate is an insecticide belonging to the organophosphates, preferably provided at a purity of 80-90%. Acephate is a colourless solid with a melting point of 82-89° C. having a solubility at room temperature with about 650 g/l water; >100 g/l acetone; ethanol; <50 g/l aromatic solvents. Acephate has the structural formula as follows:

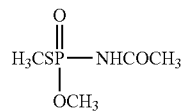

In a preferred embodiment, the insecticidal composition includes the following:

| | |
|---|---|
| (i) Cypermethrin (active ingredient) | 0.1-25% |
| (ii) Acephate (active ingredient) | 0.5-75% |
| (iii) Solubilizer | 0.01-10.0% |
| (iv) Emetic agent | 0.002-0.005% |
| (v) Disintegrating agent | 1.0-10.0% |
| (vi) Antifoaming agent | 0.01-0.5% |
| (vii) Wetting cum dispersing agent | 0.5-5.0% |
| (viii) Anticaking agent | 0.1-5.0% |
| (ix) Dye(s) | 0.05-0.5% |
| (x) Inert fillers | to make 100% (w/w). |

In a preferred embodiment, the insecticidal composition is prepared comprising the following steps:
1) Premixing a required quantity of Cypermethrin, preferably Cypermethrin technical, with a required quantity of a solubilizer and an emetic agent to prepare a spray solution,
2) Premixing a required quantity of Acephate, preferably Acephate technical, with a required quantity of a wetting cum dispersing agent and any other necessary additive(s) and filler(s), preferably an antifoaming agent, a disintegrating agent, an anticaking agent, dye(s) and required inert filler(s) to prepare an Acephate mixture,
3) Grinding the Acephate mixture to achieve intimate and efficient mixing of particles and then post-mixing to produce a homogeneous mixture,
4) Spraying the spray solution on the homogeneous mixture and again mixing thoroughly for sufficient time to have a homogeneous bulk,
5) Feeding the homogeneous bulk of step 4), preferably after passing quality tests, to a granulator, preferably through a screw feeder into the hopper of a granulator, for granulation to produce granules,
6) Drying, sizing and sieving the granules,
7) Optionally, recycling any fines collected after sieving to the granulator.

The granules, thus obtained, are preferably tested for required quality specifications. Once the granules pass quality specification, they are preferably filled and packed in desired packing. This process gives 99.5% yield conversion. The granules, with incorporation of inert ingredients by proper choice, enjoy all the advantages as discussed before, making it beneficial from an economic aspect and a handling aspect and shows a very good performance during application. The granules prepared as provided are dust free granules, with good pourability, stability, dispersibility, and free flowability. The granules preferably have a diameter of 0.5 mm to 1.0 mm and a length of 1.0 to 10.0 mm and having a storage stability for a minimum of two years.

The following is a list of preferred ingredients and should not be construed to limit the invention. In a preferred embodiment, the Cypermethrin used is Cypermethrin technical preferably having at least 92.5% purity. In a preferred embodiment, the Acephate used is Acephate technical preferably having a purity of at least 97%. The solubilizer is preferably a derivative of ethoxylates of vegetable oil or a mixture of one or more of these. The preferred emetic agent is a lignocaine derivative or a formulation thereof. The disintegrating agent is preferably selected from swelling type clays like beutonite, zeolite, attapulgite and inorganic salts like sodium and ammonium sulphate. The antifoaming agent is preferably a silicone oil derivative. The wetting cum dispersing agents is preferably selected from salts of alkyl sulphonates. The dye used may preferably have a sunset yellow colour. The fillers is preferably selected from precipitated silica and diatomaceous earth kaolin in the ratio 1:10 to 10:1.

EXAMPLES

The following examples are presented to illustrate but not limit the scope of the invention.

Example-1

Cypermethrin 1.0%+Acephate 50% DF granules are prepared as follows:

| Composition | Quantity (% w/w) |
|---|---|
| Acephate Tech. of 97.0% purity | 51.550 |
| Cypermethrin Tech. of 92.5% purity | 1.082 |
| Solubilizer | 0.300 |
| Emetic agent | 0.002 |
| Disintegrating agent | 2.000 |
| Antifoaming agent | 0.030 |
| Anticaking agent | 0.100 |
| Wetting cum dispersing agent | 1.000 |
| Dye(s) | 0.100 |
| Filler(s) | 43.836 |
| | 100.00% w/w |

The Cypermethrin technical was pre-mixed with the solubilizer and the emetic agent to prepare the spray solution. The Acephate Technical, the wetting cum dispersing agent, the anticaking agent, the disintegrating agent, the antifoaming agent, dye(s) and the inert filler(s) were pre-mixed and ground in a microniser to the required size. The ground product was post-mixed to get a uniform homogeneous mixture. The above spray solution was sprayed onto this homogeneous mixture and mixed to have a homogeneous bulk. This homogeneous bulk was fed through a screw feeder into the hopper of a granulator to produce granules. The granules obtained were dried and then processed for sizing and sieving to remove fines which were recycled to obtain a yield of 99%.

Example-2

Cypermethrin 5%+Acephate 25% DF Granules are prepared as follows:

| Composition | Quantity (% w/w) |
|---|---|
| Acephate tech. of 97% purity | 25.780 |
| Cypermethrin tech. of 92.5% purity | 5.410 |
| Solubilizer | 1.000 |
| Emetic agent | 0.003 |
| Disintegrating agent | 4.000 |
| Antifoaming agent | 0.040 |
| Wetting cum dispersing agent | 2.000 |
| Anticaking agent | 0.150 |
| Dye | 0.100 |
| Fillers | 61.517 |
| Total | 100.000 |

Cypermethrin 5%+Acephate 25% DF Granules with above composition are prepared by the process described in Example-1.

Example-3

Cypermethrin 10%+Acephate 10% DF Granules are prepared as follows:

| Composition | Quantity (% w/w) |
|---|---|
| Acephate tech. of 97% purity | 10.310 |
| Cypermethrin tech. of 92.5% purity | 10.820 |
| Solubilizer | 3.000 |
| Emetic agent | 0.004 |
| Disintegrating agent | 5.000 |
| Antifoaming agent | 0.050 |
| Wetting cum dispersing agent | 3.000 |
| Anticaking agent | 0.200 |
| Dye | 0.100 |
| Fillers | 67.516 |
| Total | 100.000 |

Cypermethrin 10%+Acephate 10% DF granules with above composition are prepared by following the process as described in Example-1.

Example-4

Cypermethrin 10%+Acephate 35% DF Granules are prepared as follows:

| Composition | Quantity (% w/w) |
|---|---|
| Acephate tech. of 97% purity | 36.090 |
| Cypermethrin tech. of 92.5% purity (40-80% cis-isomer) | 10.820 |
| Solubilizer | 3.000 |
| Emetic agent | 0.003 |
| Disintegrating agent | 3.000 |
| Antifoaming agent | 0.060 |
| Wetting cum dispersing agent | 3.000 |
| Anticaking agent | 0.200 |
| Dye | 0.200 |
| Fillers | 43.627 |
| Total | 100.000 |

Cypermethrin 10%+Acephate 35% DF granules with above composition are prepared by following the process as described in Example-1.

Example-5

Cypermethrin 2%+Acephate 48% DF Granules are prepared as follows:

| Composition | Quantity (% w/w) |
|---|---|
| Acephate tech. of 97% purity | 49.490 |
| Cypermethrin tech. of 92.5% purity (40-80% cis-isomer) | 2.163 |
| Solubilizer | 4.000 |
| Emetic agent | 0.004 |
| Disintegrating agent | 4.000 |
| Antifoaming agent | 0.070 |
| Wetting cum dispersing agent | 5.000 |
| Anticaking agent | 0.500 |
| Dye | 0.200 |
| Fillers | 34.573 |
| Total | 100.000 |

Cypermethrin 2%+Acephate 48% DF granules with above composition are prepared by following the process as described in Example-1.

Example-6

Cypermethrin 2.5%+Acephate 37.5% DF Granules are prepared as follows:

| Composition | Quantity (% w/w) |
|---|---|
| Acephate tech. of 97% purity | 38.660 |
| Cypermethrin tech. of 92.5% purity | 2.703 |
| Solubilizer | 1.000 |
| Emetic agent | 0.005 |
| Disintegrating agent | 5.000 |
| Antifoaming agent | 0.100 |
| Wetting cum dispersing agent | 3.000 |
| Anticaking agent | 1.000 |
| Dye | 0.150 |
| Fillers | 48.382 |
| Total | 100.000 |

Cypermethrin 2.5%+Acephate 37.5% DF granules with above composition are prepared by following the process as described in Example-1.

Example-7

Cypermethrin 5%+Acephate 45% DF Granules are prepared as follows:

| Composition | Quantity (% w/w) |
|---|---|
| Acephate tech. of 97% purity | 46.392 |
| Cypermethrin tech. of 92.5% purity | 5.410 |
| Solubilizer | 1.500 |
| Emetic agent | 0.005 |
| Disintegrating agent | 5.000 |
| Antifoaming agent | 0.100 |
| Wetting cum dispersing agent | 4.000 |
| Anticaking agent | 2.000 |
| Dye | 0.100 |
| Fillers | 35.493 |
| Total | 100.000 |

Cypermethrin 5%+Acephate 45% DF granules with above composition are prepared by following the process as described in Example-1.

Example-8

Cypermethrin 5%+Acephate 40% DF Granules are prepared as follows:

| Composition | Quantity (% w/w) |
|---|---|
| Acephate tech. of 97% purity | 41.237 |
| Cypermethrin tech. of 92.5% purity | 5.410 |
| Solubilizer | 1.500 |
| Emetic agent | 0.005 |
| Disintegrating agent | 5.000 |
| Antifoaming agent | 0.100 |
| Wetting cum dispersing agent | 4.000 |
| Anticaking agent | 2.000 |
| Dye | 0.100 |
| Fillers | 40.648 |
| Total | 100.000 |

Cypermethrin 5%+Acephate 40% DF granules with above composition are prepared by following the process as described in Example-1.

Example-9

Cypermethrin 2.5%+Acephate 40% DF Granules are prepared as follows:

| Composition | Quantity (% w/w) |
|---|---|
| Acephate tech. of 97% purity | 41.237 |
| Cypermethrin tech. of 92.5% purity | 2.703 |
| Solubilizer | 1.000 |
| Emetic agent | 0.003 |
| Disintegrating agent | 4.500 |
| Antifoaming agent | 0.500 |
| Wetting cum dispersing agent | 2.000 |
| Anticaking agent | 4.000 |
| Dye | 0.200 |
| Fillers | 43.857 |
| Total | 100.000 |

Cypermethrin 2.5%+Acephate 40% DF granules with above composition are prepared by following the process as described in Example-1.

Example-10

Cypermethrin 0.5%+Acephate 40% DF Granules are prepared as follows:

| Composition | Quantity (% w/w) |
|---|---|
| Acephate tech. of 97% purity | 41.237 |
| Cypermethrin tech. of 92.5% purity | 0.541 |
| Solubilizer | 0.250 |
| Emetic agent | 0.003 |
| Disintegrating agent | 4.000 |
| Antifoaming agent | 0.100 |
| Wetting cum dispersing agent | 5.000 |
| Anticaking agent | 5.000 |
| Dye | 0.300 |
| Fillers | 43.569 |
| Total | 100.000 |

Cypermethrin 0.5%+Acephate 40% DF granules with above composition are prepared by following the process as described in Example-1.

Experimental Detail

In the tables set forth below, the results of a series of tests show synergistic activity between the two active ingredients, Cypermethrin and Acephate, which make up the insecticidal composition.

The effects observed by comparing the extent of bollworm incidence and sucking pests population per leaf in the test fields treated with the insecticidal composition of the present invention against that occurring in untreated and individually treated fields are detailed below. The crop considered was cotton and the insects were Cotton bollworm and sucking pests

| Test-1 Details of Experiment | | |
|---|---|---|
| a) | Design | Randomized block design (RBD) |
| b) | Replications | Three |
| c) | Treatment | Nineteen (19) |
| d) | Plot size (net plot) | 4.5 × 4.2 sq. m |
| e) | Variety | NHH-44 - hybrid Cotton |
| f) | Crop | Cotton |

| | Test-1 Details of Experiment | |
|---|---|---|
| g) | Application time | Seven spray<br>i) 60 days after sowing<br>ii) 9 days after first spray<br>iii) 9 days after second spray<br>iv) 5 days after third spray<br>v) 9 days after fourth spray<br>vi) 10 days after fifth spray<br>vii) 17 days after sixth spray |
| h) | Application rate | Two litres per plot |
| i) | Untreated control plots were sprayed with the same quantity of water (i.e. 2 litres per plot) without insecticides. | |
| j) | Spray mixture used | 1000 litres/ha with knapsack sprayer |
| k) | Common sprays for early sucking pests | Two sprays |

Methodology

Sucking Pests:

Five plants per replications were selected and tagged. The number of leaf hoppers, whitefly and aphids were counted on the three leaves from each plant (3, 5 and 7th leaf on the main stem from top). Population count was made on one day before spraying and four days after spraying. The mean population per leaf per plant for all the sprays was estimated.

Bollworms:

Five plants per replication were selected and tagged. The number of fruiting bodies damaged and healthy were recorded. Observation were made on one day before spraying and four days after spraying. The percentage of fruiting bodies damaged is computed. Similarly, at picking, the number of good opened bolls (GOB) and bad opened bolls (BOB) on five tagged plants were recorded at each picking and then the mean values per plant was computed in percent.

TABLE 1

Bioefficacy of Cypermethrin + Acephate on Cotton sucking Insect pests.

| | | | Mean Pest Population leaf | | |
|---|---|---|---|---|---|
| S. No. | Treatment | Dosage of a.i. gm/Ltr | Leaf hopper | Whitefly | Aphids |
| 1 | CPN(3) + Acephate(40) 43% DF | 0.5 | 0.35 | 4.80 | 12.99 |
| 2 | CPN(3) + Acephate(43) 46% DF | 0.5 | 0.32 | 4.76 | 12.95 |
| 3 | CPN(3) + Acephate(45) 48% DF | 0.5 | 0.30 | 4.73 | 12.90 |
| 4 | CPN(3) + Acephate(47) 50% DF | 0.5 | 0.28 | 4.50 | 12.68 |
| 5 | CPN(5) + Acephate(40) 45% DF | 0.5 | 0.25 | 4.34 | 12.45 |
| 6 | CPN(5) + Acephate(43) 48% DF | 0.5 | 0.21 | 4.25 | 12.25 |
| 7 | CPN(5) + Acephate(45) 50% DF | 0.5 | 0.20 | 4.21 | 12.02 |
| 8 | CPN(5) + Acephate(47) 52% DF | 0.5 | 0.19 | 4.16 | 11.94 |
| 9 | CPN(5) + Acephate(40) 45% DF | 0.5 | 0.18 | 4.11 | 11.88 |
| 10 | CPN(7) + Acephate(43) 50% DF | 0.5 | 0.17 | 4.05 | 11.79 |
| 11 | CPN(7) + Acephate(45) 52% DF | 0.5 | 0.17 | 4.01 | 11.73 |
| 12 | CPN(7) + Acephate(47) 54% DF | 0.5 | 0.15 | 3.93 | 11.65 |
| 13 | CPN(10) + Acephate(40) 50% DF | 0.5 | 0.15 | 3.80 | 11.03 |
| 14 | CPN(10) + Acephate(43) 53% DF | 0.5 | 0.13 | 3.76 | 10.98 |
| 15 | CPN(10) + Acephate(45) 55% DF | 0.5 | 0.12 | 3.73 | 10.92 |
| 16 | CPN(10) + Acephate(47) 57% DF | 0.5 | 0.10 | 3.70 | 10.88 |
| 17 | CPN 10% EC | 0.5 | 0.70 | 7.22 | 35.30 |
| 18 | Acephate 75% SP | 0.5 | 0.58 | 4.05 | 5.70 |
| 19 | Untreated control | — | 5.72 | 6.20 | 11.35 |

CPN - Cypermethrin active ingredient
Acephate - Acephate active ingredient
EC - Emulsifiable Concentrate
SP - Soluble Powder

TABLE 2

Bioefficacy of Cypermethrin and/or Acephate DF on Cotton Bollworms.

| S. No. | Treatment | Dosage of a.i. gm/Ltr | % bollworm incidence | GOB per plant | BOB per plant |
|---|---|---|---|---|---|
| 1 | CPN(3) + Acephate(40) 43% DF | 0.5 | 18.39 | 26.1 | 10 |
| 2 | CPN(3) + Acephate(43) 46% DF | 0.5 | 18.26 | 26.3 | 9.9 |
| 3 | CPN(3) + Acephate(45) 48% DF | 0.5 | 18.11 | 26.4 | 9.5 |
| 4 | CPN(3) + Acephate(47) 50% DF | 0.5 | 18.00 | 26.9 | 9.2 |
| 5 | CPN(5) + Acephate(40) 45% DF | 0.5 | 17.92 | 27.5 | 8.7 |
| 6 | CPN(5) + Acephate(43) 48% DF | 0.5 | 17.79 | 28.19 | 8.1 |
| 7 | CPN(5) + Acephate(45) 50% DF | 0.5 | 17.73 | 29.1 | 7.9 |
| 8 | CPN(5) + Acephate(47) 52% DF | 0.5 | 17.62 | 29.3 | 7.9 |
| 9 | CPN(5) + Acephate(40) 45% DF | 0.5 | 16.98 | 29.40 | 7.7 |
| 10 | CPN(7) + Acephate(43) 50% DF | 0.5 | 16.65 | 29.6 | 7.6 |
| 11 | CPN(7) + Acephate(45) 52% DF | 0.5 | 16.23 | 29.8 | 7.5 |
| 12 | CPN(7) + Acephate(47) 54% DF | 0.5 | 15.71 | 29.9 | 7.4 |
| 13 | CPN(10) + Acephate(40) 50% DF | 0.5 | 15.20 | 30.1 | 7.4 |
| 14 | CPN(10) + Acephate(43) 53% DF | 0.5 | 14.72 | 30.2 | 7.3 |
| 15 | CPN(10) + Acephate(45) 55% DF | 0.5 | 14.19 | 30.3 | 7.3 |

TABLE 2-continued

Bioefficacy of Cypermethrin and/or Acephate DF on Cotton Bollworms.

| S. No. | Treatment | Dosage of a.i. gm/Ltr | % bollworm incidence | GOB per plant | BOB per plant |
|---|---|---|---|---|---|
| 16 | CPN(10) + Acephate(47) 57% DF | 0.5 | 13.88 | 30.7 | 7.0 |
| 17 | CPN 10% EC | 0.5 | 28.05 | 24.8 | 10.2 |
| 18 | Acephate 75% SP | 0.5 | 28.05 | 25.5 | 10.2 |
| 19 | Untreated control | — | 41.77 | 11.8 | 14.6 |

CPN - Cypermethrin active ingredient
Acephate - Acephate active ingredient
EC - Emulsifiable Concentrate
SP - Soluble Powder.

The test results of all the formulated product samples reveals that the samples could be classified into four groups according to their efficiency.

Group A (Grade-1)
1. Cypermethrin (5)+Acephate (45) DF(w/w)
2. Cypermethrin (3)+Acephate (47) DF(w/w)
3. Cypermethrin (7)+Acephate (47) DF(w/w)
4. Cypermethrin (5)+Acephate (47) DF(w/w)
5. Cypermethrin (7)+Acephate (45) DF(w/w)
6. Cypermethrin (7)+Acephate (43) DF(w/w)
7. Cypermethrin (7)+Acephate (40) DF (w/w)

Group-B (Grade II)
1. Cypermethrin (5)+Acephate (43) DF(w/w)
2. Cypermethrin (5)+Acephate (45) DF(w/w)
3. Cypermethrin (3)+Acephate (45) DF(w/w)

Group-C (Grade III)
1. Cypermethrin (3)+Acephate (43) DF(w/w)
2. Cypermethrin (3)+Acephate (40) DF(w/w)

Group-D (Grade-IV)
Untreated

Result

Out of Grade-I results in group A, the concentration of Cypermethrin (5)+Acephate (45) DF (w/w) earns the preference on the others due to low residual value, lower loading of toxicant/ha, without compromising the preferred results.

Advantages

The selected synergistic insecticidal composition of Cypermethrin (5.0)+Acephate (45) DF (w/w) has:
  low residual value;
  lower loading of toxicant/ha to achieve same results; and
  good effect in controlling cotton bollworm and sucking pests.

The insecticidal composition of the present invention is very effective against Cotton bollworms, leaf hoppers, whitefly and aphids, when used in 1:9 ratio of Cypermethrin:Acephate (on active ingredient basis) due to synergic activity. The DF (dry flow) granules on addition to water disperse the active content easily. The suspension prepared exhibits good stability which helps in uniform distribution of active ingredient on plants when applied. And, the granules are safe for humans and animals.

Conclusion

The overall results and observation from Table 1 and 2 shows that Cypermethrin (5)+Acephate (45) DF (w/w) show a good synergistic property in comparison to existing formulations of Cypermethrin and Acephate individually.

Test-2

The following is an evaluation of Cypermethrin (5)+Acephate (45) DF (w/w) ready mix against cotton insect pests.

Details of the Experiment

| | | |
|---|---|---|
| a) | Design | R.B.D |
| b) | Replications | Three |
| c) | Treatments | Twelve |
| | | 1) Cypermethrin 5% DF (at 50 g. a.i./ha) |
| | | 2) Cypermethrin 5% DF (at 60 g a.i./ha) |
| | | 3) Cypermethrin 5% DF (at 70 g a.i./ha) |
| | | 4) Cypermethrin (5) + Acephate(45) DF (w/w) (at 400 g a.i./ha) |
| | | 5) Cypermethrin (5) + Acephate(45) DF (w/w) (at 425 g a.i.ha) |
| | | 6) Cypermethrin(5) + Acephate (45) DF(w/w) (at 450 g. a.i./ha) |
| | | 7) Acephate 75% DF (at 550 g a.i./ha) |
| | | 8) Acephate 75% DF (at 575 g. a.i./ha) |
| | | 9) Acephate 75% DF ( at 585 g a.i./ha) |
| | | 10) Cypermethrin 25% EC (at 60 g a.i./ha) |
| | | 11) Acephate 75% SP (at 575 g a.i./ha) |
| | | 12) Untreated Control |
| d) | Plot size (net plot) | 4.5 × 4.2 sq. m |
| e) | Variety | NHH-44 hybrid Cotton |
| f) | No. of spraying | Seven sprays |
| | | 1) 60 days after sowing |
| | | 2) 8 days after first spray |
| | | 3) 8 days after second spray |
| | | 4) 5 days after third spray |
| | | 5) 8 days after fourth spray |
| | | 6) 10 days after fifth spray |
| | | 7) 20 days after sixth spray |
| g) | Spray mixture used | 1000 l/ha with Knapsack sprayer |
| h) | Common sprays for early Sucking pests. | Two sprays with systemic insecticides. |

Methodology:

Sucking Pests:

Five plants per replications were selected and tagged. The number of leaf hoppers, whiteflies and aphids were counted on 3 leaves from each plant (3, 5 and 7th leaf on the main steam from top). Population count was made on one day before spraying and four days after spraying. The mean population per leaf per plant for all sprays was estimated.

Bollworms:

Five plants per replications were selected and tagged. The number of fruiting bodies damaged and healthy were recorded. Observations were made on one day before spraying and four days after spraying. The percentage of fruiting bodies damaged is computed.

Similarly at the picking, the number of good opened bolls and bad opened bolls on five tagged plants, were recorded at each picking.

Cotton yield per plot was recorded separately and it was computed to quintal/ha.

Results

Sucking Insect Population:

All the various treatment dosages of Cypermethrin 5% DF, Acephate 75% DF and Cypermethrin (5)+Acephate (45) DF, reduced leafhopper population and they were at par with each other. Untreated control recorded a maximum of 5.72 leaf hopper per leaf.

All the dosage levels of Acephate 75% DF and Cypermethrin+Acephate ready mix combination recorded lower population of whiteflies and they were at par with each other and also Acephate 75% SP treatment. Whereas, all the dosage level treatments of Cypermethrin 5% DF and Cypermethrin 25% EC were comparable to untreated control in recording whiteflies population. Minimum aphid population was recorded in all the dosage treatments of Acephate 75% DF and Acephate 75% SP insecticide. Whereas, Cypermethrin 5% DF and 25% EC treatments recorded relatively high population of aphids. In Cypermethrin+Acephate ready mix, aphid population was significantly less than the Cypermethrin treatment alone because of the inclusion of Acephate. But these treatments were comparable to untreated control which recorded 11.35 aphids per leaf. (Table-3)

Percent Bollworm Incidence:

All the dosage level treatments of Cypermethrin+Acephate ready mix recorded lower percent bollworm incidence and they were at par with each other and significantly superior over the rest of the treatments. Treatments of Cypermethrin 5% DF alone at 70 g a.i./ha treatment recorded 27.02% bollworm incidence which was significantly superior over its lower dosage treatments and also Cypermethrin 25% EC and Acephate 75% SP treatments. Untreated control recorded a maximum of 41.77 percent bollworm incidence. (Table-4)

GOB and BOB per Plant:

Maximum number of GOBs and minimum number of BOBs per plant were recorded in all the dosage level treatments of Cypermethrin+Acephate ready mix treatments and these treatments were significantly superior over other treatments. Treatments of Cypermethrin 5% DF alone at 70 g a.i./ha treatment recorded 25.0 GOBs and 10 BOBs per plant respectively which was superior to its lower dosage treatments but comparable to all the dosage level treatments of Acephate 75 DF and SP treatments. Untreated control recorded 11.8 and 14.6 GOB and BOB per plant respectively. (Table-4)

Yield:

Ready mix treatment of Cypermethrin (5)+Acephate (45) DF at all the dosage levels recorded relatively higher seed cotton yield and the treatments were significantly superior over other treatments. Cypermethrin at 60 g a.i./ha treatments recorded 10.45 q/ha seed cotton which was at par with its higher dosage treatments but superior to its lower dosage treatments, whereas Acephate 75% DF at 575 g a.i.ha treatment recorded 11.42 q/ha seed cotton yield which was at par with both its higher as well as lower dosage treatments and also comparable standard check treatments. Untreated control recorded a minimum of 6.38 q/ha seed cotton yield. (Table-4)

Conclusion:

All the dosage level treatments of Cypermethrin (5)+Acephate (45) DF recorded lowest percent bollworm damage and higher cotton yield than alone treatments of Cypermethrin 5% DF and Acephate 75% DF singly. Cypermethrin 5% DF at 70 g a.i./ha treatment was comparable to all the dosage level treatments of Acephate 75% DF.

TABLE 3

Bioefficacy of Cypermethrin 5% DF and Cypermethrin 5% DF + Acephate 45% DF ready mix against cotton sucking insect pests.

| Sr. No. | Treatments | Dosage a.i. gm/ha | Leaf hoppers | White-flies | Aphids |
|---|---|---|---|---|---|
| 1 | Cypermethrin 5% DF | 50 | 0.65 a | 6.75b | 28.80c |
| 2 | Cypermethrin 5% DF | 60 | 0.60a | 9.10b | 30.12c |
| 3 | Cypermethrin 5% DF | 70 | 0.52a | 6.80b | 28.25c |
| 4 | Cypermethrin 5% DF + Acephate 45% | 400 | 0.35a | 3.85a | 14.35b |
| 5 | Cypermethrin 5% + Acephate 45% | 425 | 0.40a | 4.12a | 12.70b |
| 6 | Cypermethrin 5% + Acephate 45% | 450 | 0.22a | 4.35a | 12.38b |
| 7 | Acephate 75% DF | 550 | 0.38a | 4.70a | 6.75a |
| 8 | Acephate 75% DF | 575 | 0.30a | 4.15a | 6.00a |
| 9 | Acephate 75% DF | 585 | 0.25a | 3.72a | 5.80a |
| 10 | Cypermethrin 25% EC | 60 | 0.70a | 7.22b | 35.30d |
| 11 | Acephate 75% WP | 575 | 0.58a | 4.05a | 5.70a |
| 12 | Untreated control | — | 5.72b | 6.20b | 11.35b |
| SEm ± | | | 0.28 | 0.35 | 1.38 |
| CS at 5% level | | | 0.85 | 1.10 | 4.12 |

TABLE 4

Bioefficacy of Cypermethrin 5% DF and Cypermethrin 5% DF + Acephate 45% readymix against bollworm incidence and cotton yield.

| Sr. No | Treatment | Dosage ai/ha | % bollworm incidence | GOB per plant | BOB per plant | Cotton yield (q/ha) |
|---|---|---|---|---|---|---|
| 1 | Cypermethrin 5% DF | 50 | 32.47 (34.71)e | 18.7b | 14.2cd | 9.12b |
| 2 | Cyermethrin 5% DF | 60 | 29.05 (32.55)d | 21.9c | 12.7c | 10.45c |
| 3 | Cypermethrin 5% DF | 70 | 27.02 (31.32)bc | 25.0d | 10.0ab | 11.20cd |
| 4 | Cypermethrin 5% + Acephate 45% | 400 | 20.02 (26.70)a | 28.8e | 9.2ab | 12.85e |
| 5 | Cypermethrin 5% + Acephate 45% | 425 | 19.60 (26.28)a | 29.6e | 9.0a | 13.10e |
| 6 | Cypermethrin 5% + Acephate 45% | 450 | 18.95 (25.78)a | 30.2e | 8.6a | 13.34e |
| 7 | Acephate 75% DF | 550 | 28.12 (32.02)cd | 24.7cd | 10.8b | 11.10cd |
| 8 | Acephate 75% DF | 575 | 27.14 (31.36)bc | 25.0d | 10.3ab | 11.42d |

TABLE 4-continued

Bioefficacy of Cypermethrin 5% DF and Cypermethrin 5% DF + Acephate 45% readymix against bollworm incidence and cotton yield.

| Sr. No | Treatment | Dosage ai/ha | % bollworm incidence | GOB per plant | BOB per plant | Cotton yield (q/ha) |
|---|---|---|---|---|---|---|
| 9 | Acephate 75% DF | 585 | 26.30 (30.85)b | 25.5d | 9.8ab | 11.84d |
| 10 | Cypermethrin 25% EC | 60 | 28.50 (32.22)cd | 24.8d | 10.2ab | 11.17cd |
| 11 | Acephate 75% WP | 575 | 28.05 (31.97)cd | 25.5cd | 10.2ab | 10.95cd |
| 12 | Untreated control | — | 41.77 (40.25)f | 11.8a | 14.6d | 6.38a |
|  | SEm ± |  | 0.37 | 0.9 | 0.5 | 0.32 |
|  | CD at 5% level |  | 1.10 | 2.8 | 1.7 | 0.94 |

Figures in the parentheses are angular transformed values.

The synergistic effect which is the base of the present insecticidal composition has been demonstrated by way of results. The effect is described as follows.

The mentioned numbers for cash component—Cypermethrin+Acephate corresponds to % grams/kg in the formulation in three different concentration (4+36; 5+45; 6+54) all in % g/kg were tested using same operating condition as described in example 11, 12 except variation in active ingredient in the ratio (by weight) of 1:9 (i.e. 5:95 in parts of a.i. Cypermethrin:Acephate).

| Crop: | Cotton |
|---|---|
| Sort of Pest: | a. Bollworm (Cotton Crop) |
|  | b. Jassid. |

Experiment-1

Percentage of Incidence after Spraying

|  | % of incidence | |
|---|---|---|
| Concentration (w/w) | Bollworm | Jassid |
| Cypermethrin 4% + Acephate 36% | 25.03 | 16.24 |
| Cypermethrin 5% + Acephate 45% | 18.95 | 11.73 |
| Cypermethrin 6% + Acephate 54% | 16.71 | 10.89 |

Experiment-2

|  | % of incidence | |
|---|---|---|
| Concentration (w/w) | Bollworm | Jassid |
| Cypermethrin 4% + Acephate 36% | 26.27 | 17.03 |
| Cypermethrin 5% + Acephate 45% | 19.40 | 12.46 |
| Cypermethrin 6% + Acephate 54% | 17.92 | 11.31 |

Conclusion

|  | Performance | | |
|---|---|---|---|
| Concentration (w/w) | Bollworm | Jassid | Crop Residual |
| Cypermethrin 4% + Acephate 36% | + | + | BDL |
| Cypermethrin 5% + Acephate 45% | +++ | +++ | BDL |
| Cypermethrin 6% + Acephate 54% | +++ | +++ | Trace |

+: Normal
++: Good
+++: Very Good
BDL: Below detectable level

The above experiment on the Cotton for bollworms and Jassids established that Cypermethrin (5)+Acephate (45) DF & Cypermethrin (6)+Acephate (54) DF showed comparable efficiency in controlling bollworms and Jassids, whereas Cypermethrin (4)+Acephate (36) DF showed normal results at the given dosage per hectare.

From the above test 3, it is concluded that Cypermethrin (5)+Acephate (45) DF is very effective when compared to higher concentration combinations as it is evident that the higher concentration combination does not exhibit any considerable improvement in effectiveness but only adds to unnecessary, excess use of active ingredient causing environmental pollution.

The minimum dosage of Cypermethrin (5)+Acephate (45) DF depends upon the type and the evaluation of the field of cultivation. The experiments conducted make it possible to recommend the following initial doses.

|  |  | Dose gm/ha | | Waiting period |
|---|---|---|---|---|
| Crop | Pest (type of culture) | a.i. | DF | in days |
| Cotton | American bollworm Spotted bollworm Jassids | 400–450 | 800–900 | 15 days | a.i.—active ingredient
DF—Dry flowable granules

Test:-4

Phytotoxicity Studies on Cotton

Observations taken for ten days on necrosis, epinasty, hyponesty, leaf lip injury, leaf surface injury, vein clearing etc. for evaluation of Cypermethrin (5)+Acephate (45) DF readymix, Cypermethrin 5% DF and Acephate 75 DF and SP for phytotoxicity on cotton.

TABLE 5

| Sr. No. | Treatments | Dosage (g a.i./ha) | Visual rating (Pytotoxicity) in 1-10 scale of grading | | | | | | | | | |
|---|---|---|---|---|---|---|---|---|---|---|---|---|
| | | | 1 1-10% | 2 11-20% | 3 21-30% | 4 31-40% | 5 41-50% | 6 51-60% | 7 61-70% | 8 71-80% | 9 81-90% | 10 91-100% |
| 1 | Cypermethrin 5% DF | 50 | NP | NP | NP | NP | NP | NP | NP | NP | NP | NP |
| 2 | Cypermethrin 5% DF | 60 | NP | NP | NP | NP | NP | NP | NP | NP | NP | NP |
| 3 | Cypermethrin 5% DF | 70 | NP | NP | NP | NP | NP | NP | NP | NP | NP | NP |
| 4 | Cypermethrin 5% DF + Acephate 45% | 400 | NP | NP | NP | NP | NP | NP | NP | NP | NP | NP |
| 5 | Cypermethrin 5% + Acephate 45% | 425 | NP | NP | NP | NP | NP | NP | NP | NP | NP | NP |
| 6 | Cypermethrin 5% + Acephate 45% | 450 | NP | NP | NP | NP | NP | NP | NP | NP | NP | NP |
| 7 | Acephate 75% DF | 550 | NP | NP | NP | NP | NP | NP | NP | NP | NP | NP |
| 8 | Acephate 75% DF | 575 | NP | NP | NP | NP | NP | NP | NP | NP | NP | NP |
| 9 | Acephate 75% DF | 585 | NP | NP | NP | NP | NP | NP | NP | NP | NP | NP |
| 10 | Cypermethrin 25% EC | 60 | NP | NP | NP | NP | NP | NP | NP | NP | NP | NP |
| 11 | Acephate 75% WP | 575 | NP | NP | NP | NP | NP | NP | NP | NP | NP | NP |
| 12 | Untreated control | — | NP | NP | NP | NP | NP | NP | NP | NP | NP | NP |

Note:
Observations taken for ten days on necrosis, epinasty, hypenasty, leaft tip injury, leaf surface injury, vein cleaning etc.
NP = No Pytotoxicity Results:

There were no visible phytoxicity symptoms on Cotton Plants treated with various dosage level treatment of Cypermethrin (5)+Acephate (45) 50% DF, Cypermethrin 5% DF, Acephate 75% DF & SP insecticides.

Inference:

From the above examples, it is concluded that Cypermethrin+Acephate exhibits synergistic insecticidal activity in the range of 1:1 to 1:10 (Cypermethrin:Acephate) dosage per hectare, the most preferable being 1:9. This ratio demonstrates the optional synergistic activity and is very effective against cotton bollworm, leaf hopper and sucking pest. This dosage ratio of active ingredients is significantly less than that required when Cypermethrin and Acephate are applied individually for achieving the same performance. The present insecticidal composition reduces the chances of resistance development and acts as a potent weapon to kill these insects. The formulated insecticidal composition described in the above examples and prepared by the process given in the examples 1 to 10, provides uniform distribution of the active ingredients on treated plants.

Although the present invention has been disclosed in terms of a preferred embodiment, it will be understood that numerous additional modifications and variations could be made thereto without departing from the scope of the invention as defined by the following claims:

We claim:

1. A method of treating a plant comprising, mixing a granular insecticidal composition comprising granules having a diameter of 0.5 mm to 1.0 mm and a length of 1.0 to 10.00 mm of:
   a) 3 to 10% w/w Cypermethrin;
   b) 40-47% w/w Acephate;
   c) 0.01 to 10.0% w/w a solubilizer;
   d) 0.002 to 0.005% w/w an emectic agent;
   e) 1.0 to 10.0% w/w a disintegrating agent;
   f) 0.01 to 0.5% w/w an antifoaming agent;
   g) 0.5 to 5.0% w/w a wetting cum dispersing agent;
   h) 0.1 to 5.0% w/w an anticaking agent
   i) 0.05 to 0.5% w/w a dye; and
   j) an inert filler to make 100% w/w
wherein Cypermethrin and Acephate are the only insecticidally active ingredients in said granular insecticidal composition, with water to form a suspension, and
   applying said suspension to a plant to reduce the amount of pests present on the plant.

2. The method of claim 1 comprising Cypermethrin having 45-80% of cis isomers.

3. The method of claim 1, comprising about 5% w/w Cypermethrin and about 45% w/w Acephate.

4. The method of claim 1, wherein the solubilizer is an ethoxylate of vegetable oil or a mixture thereof.

5. The method of claim 1, wherein the emetic agent is a lignaocaine derivative or a formulation thereof.

6. The method of claim 1, wherein the disintegrating agent is a swelling type clay selected from the group consisting of bentonite, zeolite, and attapulgite or an inorganic salt selected from the group consisting of sodium sulphate and ammonium sulphate.

7. The method of claim 1, wherein the antifoaming agent is a silicone oil derivative or a combination thereof.

8. The method of claim 1, wherein the wetting cum dispersing agent is a salt of alkyl aryl sulphonate.

9. The method of claim 1, wherein the anticaking agent is anhydrous magnesium sulphate.

10. The method of claim 1, wherein the filler is selected from the group consisting of precipitated silica and diatomaceous earth kaolin.

11. The method of claim 10, wherein the precipitated silica and diatomaceous earth kaolin are present in a ratio of 1:10 to 10:1.

12. The method of claim 1, wherein said granular insecticidal composition is a granule having a diameter of 0.5 mm to 1.0 mm and a length of 1.0 to 10.00 mm.

* * * * *